United States Patent [19]

Jäger

[11] 4,044,075
[45] Aug. 23, 1977

[54] DIALKYLPHOSPHONOPROPIONIC ACID AMIDES AND PROCESS FOR THEIR MANUFACTURE

[75] Inventor: Horst Jäger, Bettingen, Switzerland

[73] Assignee: Ciba-Geigy Corporation, Ardsley, N.Y.

[21] Appl. No.: 639,320

[22] Filed: Dec. 10, 1975

[30] Foreign Application Priority Data

Dec. 20, 1974 Switzerland .................. 17036/74

[51] Int. Cl.$^2$ .............................................. C07F 9/40
[52] U.S. Cl. ..................................... 260/943; 260/968
[58] Field of Search ............................... 260/943, 968

[56] References Cited
U.S. PATENT DOCUMENTS 3,801,678  4/1974  Nachbur et al. .................. 260/943

Primary Examiner—James R. Hoffman

Attorney, Agent, or Firm—Karl F. Jorda; Edward McC. Roberts; Prabodh I. Almaula

[57] ABSTRACT

Dialkylphosphonopropionic acid amides of formula

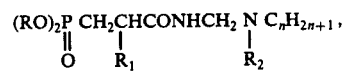

wherein R is a straight-chain or branched alkyl radical of 1 to 8 carbon atoms, $R_1$ is hydrogen or methyl, $R_2$ is hydrogen or $C_nH_{2n+1}$ and $n$ is an integer from 1 to 24, are provided. These compounds are useful for finishing synthetic organic fibrous material, in particular for providing it with an antistatic finish and optionally for simultaneously improving the dirt repellency, when applied in admixture with further monomeric compounds or with polymers; said compounds or mixtures are applied to the fibrous material from aqueous or organic preparations and the fibrous material is subsequently dried at elevated temperature.

9 Claims, No Drawings

DIALKYLPHOSPHONOPROPIONIC ACID AMIDES AND PROCESS FOR THEIR MANUFACTURE

It is known to provide synthetic organic fibrous materials with an antistatic or also dirt repellent finish. It is also known that a marked deterioration of the antisoiling effect occurs in many antistatic finishes. Another frequently observed disadvantage of the finished fibrous materials is the poor resistance to yellowing on exposure to light and/or heat.

According to the present invention there are provided new compounds with antistatic properties which, when mixed with certain monomeric or polymeric compounds, substantially overcome the disadvantages referred to above.

The present invention therefore provides dialkylphosphonopropionic acid amides of formula

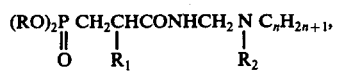
(1)

wherein R is a straight-chain or branched alkyl radical of 1 to 8 carbon atoms, $R_1$ is hydrogen or methyl, $R_2$ is hydrogen or $C_nH_{2n+1}$ and $n$ is an integer from 1 to 24.

The invention also provides a process for the manufacture of compounds of formula (1) as well as a method of using these compounds for finishing synthetic organic fibrous material, in particular for providing it with an antistatic finish and optionally for simultaneously improving the dirt repellency, optionally in admixture with further monomeric compounds or with polymers, said compounds or mixtures being applied to the fibrous material from aqueous or organic preparations, for example solutions or emulsions, and subsequently dried at elevated temperature.

In addition, the invention also provides the preparations for carrying out the method of application.

The substituent R in the substituted β-(dialkylphosphono)propionic acid amides of formula (1) is a straight-chain or branched alkyl radical of 1 to 18 carbon atoms, but alkyl radicals of 1 to 4 carbon atoms are preferred, for example methyl, ethyl, propyl, isopropyl, butyl or isobutyl.

Examples of further alkyl radicals are: amyl, hexyl, octyl, decyl, dodecyl, myristyl, palmityl or stearyl. The substituent $R_2$ is hydrogen or the alkyl radical $C_nH_{2n+1}$ and $n$ is an integer from 1 to 24, in particular from 6 to 24 and preferably from 6 to 18 or 8 to 18.

Preferred compounds of formula (1) have the formula

(2)

wherein $R_3$ is alkyl of 1 to 4 carbon atoms, $R_1$ is hydrogen or methyl, $R_4$ is hydrogen, methyl or the radical $C_{n_1}H_{2n_1+1}$ and $n_1$ is an integer from 6 to 24.

Particularly suitable compounds are also those of formulae

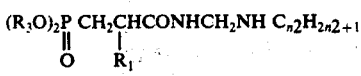
(3a)

and

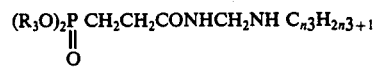
(3b)

wherein $R_1$ and $R_3$ are as defined hereinbefore, $n_2$ is an integer from 6 to 18 and $n_3$ is an integer from 8 to 18.

The compounds of formula (1) are obtained by reacting metholylated β-(dialkylphosphono)-propionic acid amides of formula

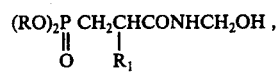
(4)

wherein R and $R_1$ are as defined hereinbefore, with mono- or dialkylamines which contain 1 to 24 carbon atoms in the alkyl moiety, at elevated temperature.

Compounds of formula (2) are obtained by reacting metholylated β-(dialkylphosphono)-propionic acid amides of formula

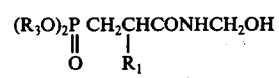
(5)

with monoalkylamines of 6 to 24 carbon atoms or with methylalkylamines the alkyl moiety of which contains 6 to 24 carbon atoms, in corresponding manner.

The particularly preferred compounds of formulae (3a) and (3b) are obtained by reacting β-(dialkylphosphono)-propionic acid amides of formula

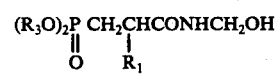
(6)

or

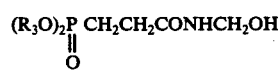
(7)

with monoalkylamines of 6 to 18 or 8 to 18 carbon atoms.

The metholylated β-(dialkylphosphono)-propionic acid amides used as starting compounds are obtained by known methods, for example by addition of dialkylphosphites to (meth)acrylic acid amides and subsequent methylolation.

The manufacture of the compounds of the present invention of formula (1) can be carried out without solvents or in organic solvents, optionally also in organic-aqueous systems, by reacting the starting materials at 80° to 120° C. The reaction time can be from about 3 to 24 hours. Examples of suitable solvents are: halogenated hydrocarbons, such as tetrachloromethane, perchloroethylene, trichloroethylene, ethers, such as dioxan, or conventional aromatic solvents, for example benzene, toluene or xylene. The solvents can contain up to 20% of water, referred to their volume.

The compounds of formula (1) are suitable antistatic agents for finishing synthetic organic fibrous materials. Because of their surface-active properties, they can also be used as non-corrosive antistatic lubricants or as detergents, for example for removing non-fixed dye from substrates that are dyed from solvents. The compounds of this invention optionally can be used in combination with compounds of formula

  (8)

wheren R' is

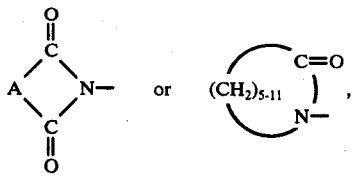

in which A is —CH$_2$—CH$_2$—, —CH=CH— or

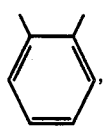,

R$_2$ is hydrogen or C$_n$H$_{2n+1}$ and n is an integer from 1 to 24, whereby it is possible to obtain improved antistatic effects without a simultaneous deterioration in the antisoiling properties of the finished material. The integer n can be in particular 6 to 24, preferably 6 to 18 or 8 to 18. R$_2$ is preferably hydrogen, and also methyl or C$_n$H$_{2n+1}$, in which n is an integer in the preferred range already indicated.

The compounds of formula (8) are succinimides, maleinimides, phthalimides or lactams, for example caprolactams or laurinolactams. Preferred compounds are those of formula

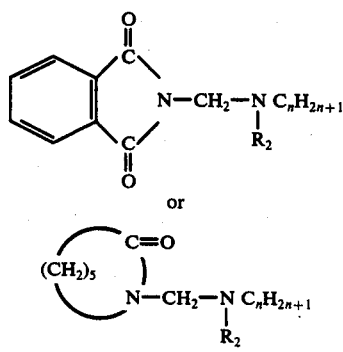

wherein R$_2$ and n are as defined hereinbefore.

The compounds of formula (8) are obtained by known methods by addition of formaldehyde to succinimides, maleinimides, phthalimides or to lactams containing 5 to 11 —CH$_2$— groups in the heterocyclic ring, especially to phthalimide or caprolactam, and subsequent reaction with mono- or dialkylamines which contain 1 to 24 carbon atoms in the alkyl moiety. Examples of amines are laurylamine of 12 carbon atoms and cetylamie of 16 carbon atoms, and dilauryl-, distearyl- and di-2-ethylhexylamine.

The imides and lactams cited as starting materials are known chemical compounds.

The compounds of the present invention can be used in the finishing methods referred to herein optionally in mixtures with at least one homopolymer derived from monomers of formula

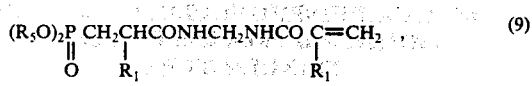  (9)

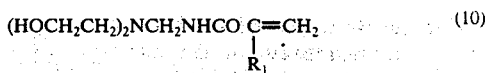  (10)

and

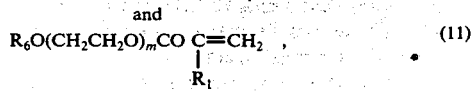  (11)

wherein R$_5$ is a straight-chain or branched alkyl radical of 1 to 8 carbon atoms, R$_1$ is hydrogen or methyl, R$_6$ is alkyl of 1 to 6 carbon atoms and m is an integer from 6 to 15, preferably 6 to 10, and optionally, with further homo- or copolymers.

The further homo- or copolymers are not derived from monomers of the formulae (9) to (11).

R$_5$ and R$_6$ are in particular alkyl of 1 to 4 carbon atoms, preferably methyl and ethyl. The homo- and copolymers can have molecular weights of about 2000 to 50, 000. 50000.

The monomers of formulae (9) to (11) are known compounds. The compounds of formula (9) are known, for example, from Swiss Pat. No. 445,126, those of formula (10) from German Auslegeschrift 1.111.825 and those of formula (11) from U.S. Pat. No. 2,839,430.

Preferred mixtures are those of compounds of formula (1) with homopolymers derived from the monomers of formulae (9), (10) and (11). The mixtures contain as a rule up to about 30 percent by weight of compounds of formula (1), optionally up to about 30 percent by weight of the compounds of formula (8) and at least 70, optionally at least 40, percent by weight of the homo- or copolymers. Preferably the monomers are used in amounts of 5 to 20 percent by weight and the polymers in amounts of 80 to 95 and 60 to 90 percent by weight respectively.

Particularly preferred monomers of formula (9) for obtaining the homopolymers are those which have for example the formulae

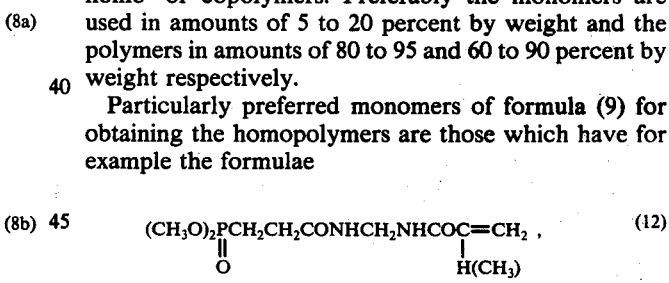

(12)

(13)

(14)

or

  (15)

Examples of preferred compounds of formulae (10) and (11) are those of formulae

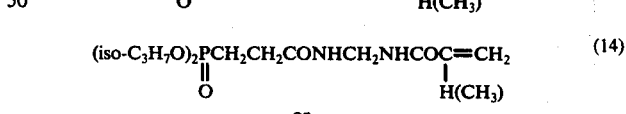  (16)

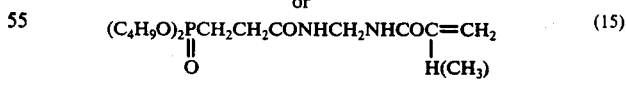  (17a)

and

-continued $$CH_3O(CH_2CH_2O)_{10-15}CO\underset{H(CH_3)}{C}=CH_2. \quad (17b)$$

Examples of suitable monomers for the manufacture of further homo- or copolymers that can be optionally used are:

a. vinyl esters of organic acids, for example vinyl acetate, vinyl formiate, vinyl butyrate, vinyl benzoate,
b. vinyl alkyl ketones, such as vinyl methyl ketone,
c. vinyl halides, such as vinyl chloride, vinyl fluoride, vinylidene chloride.
d. derivatives of the acrylic acid series, such as acrylic nitrile or acrylic amide and preferably derivatives thereof which are substituted at the amide nitrogen, for example N-methylolacrylic amide, N-methylolacrylic amide alkyl ethers, for example methylolacrylic amide monomethyl ether, N,N-dihydroxy-ethylacrylic amide, N-tert.butylacrylic amide and hexamethylolmelamine triacrylic amide, and
e. $\alpha,\beta$-unsaturated mono- or dicarboxylic acids containing 3 to 5 carbon atoms and esters thereof, for example acrylic acid, methacrylic acid, $\alpha$-chloroacrylic acid, crotonic acid, maleic acid, fumaric acid, or itaconic acid and esters thereof with mono- or dialcohols containing 1 to 18 carbon atoms, epoxides or phenols, for example ethyl acrylate, methylmethacrylate, glycidyl acrylate, butylacrylate, isobutylacrylate, acrylic acid monoglycol ester, dodecylacrylate or 2-ethyl-hexylacrylate.

Polymerisable olefins, such as isobutylene, butadiene or 2-chlorobutadiene can also be used.

It is preferred to use acrylic acid, methacrylic acid, the esters thereof with 1 to 8 carbon atoms in the ester moiety, for example methylmethacrylate, isobutylacrylate, 2-ethylhexylacrylate, as well as acrylic amide and methacrylic amide, which can be N-methylolated and optionally etherified, for example N-methylolacrylic amide, N-methylolacrylic amide methyl ether.

The manufacture of the polymers by homo- or copolymerisation is effected by conventional methods, for example preferably by polymerisation in aqueous emulsion or also by solvent polymerisation in a solvent suitable for this purpose, for example acetone, benzene, sym. dichloroethane, ethyl acetate or trifluoromethylbenzene.

The polymerisation is effected advantageously with the application of heat, preferably to the boiling temperature of the solvent, and accompanied by the addition of peroxide or other catalysts which form free radicals and which are soluble in the reaction medium, for example benzoyl peroxide, lauroyl peroxide, $\alpha,\alpha'$-azobisisobutyrodinitrile or potassium persulphate or in redox systems, for example potassium peroxide disulphate/sodium bisulphite or ferrosulphate. In the manufacture of copolymers, the monomers can be used in the polymerisation reaction in any desired quantity ratios. In the manufacture of copolymers from, for example, monomer components, the molar ratio can be for example 1:10 to 10:1, preferably 1:5 to 5:1.

Depending on the nature of the polymerisation conditions and of the monomeric starting materials used, the polymer compounds are obtained in the form of viscous solutions or of emulsions.

The polymerisation is preferably carried out within a reaction time that is so chosen that a virtually quantitative conversion of the monomer into the polymer is attained. The maximum reaction time depends on the catalyst used and the polymerisation temperature and also on other conditions, but it is generally in the range of 0.5 to 24 hours.

The polymerisation temperature depends in turn on the chosen catalyst. In the case of emulsion polymerisation in aqueous medium it is usually in the range of 20° to 90° C, preferably 40° to 80° C. Wherever possible, the polymerisation is carried out at atmospheric pressure.

In emulsion polymerisation the monomer or monomers to be polymerised are polymerised jointly in an aqueous solution of an emulsifier, optionally under nitrogen.

The concentration of the polymerisation catalyst is usually between 0.1 and 2%, referred to the weight of the monomers.

Suitable emulsifiers are cationic, anionic or non-ionic surface-active agents. The hydrophobic constituent of the emulsifier can be a hydrocarbon or a fluorinated hydrocarbon.

Suitable cationic emulsifiers are, for example, quaternary ammonium salts or amine salts which contain at least one long-chain alkyl or fluoroalkyl group, or a benzene or naphthalene group which is highly substituted by alkyl to yield the hydrophobic constituent.

Further suitable emulsifiers are the non-ionic surfactants in which the hydrophilic constituent is a poly(ethoxy) group and the hydrophobic constituent is either a hydrocarbon or a fluroinated hydrocarbon group, e.g. the ethylene oxide condensates of alkylphenols, alkanols, alkylamines, alkylthiols, alkylcarboxylic acids, fluoroalkylcarboxylic acids, fluoroalkylamides and the like. Anionic emulsifiers are, for example, the sulphuric acid or phosphoric acid esters of the cited ethylene oxide condensates of long-chain alkylphenols, fatty alcohols, and fatty amines.

In the solvent polymerisation, the monomer or monomers are dissolved in a suitable solvent, such as fluorinated solvents, for example hexafluoroxylene, benzotrifluoride, or mixtures thereof with acetone and/or ethyl acetate, and polymerised in a reaction vessel with the addition of initiators, as azobisisobutyronitrile or other azo initiators, in concentrations of 0.1 to 2%, at 40° to 100° C optionally under nitrogen.

Preferred solvents are hexafluoroxylene, benzotrifluoride or fluorinated hydrocarbons.

The preparations or compositions for the application of the compounds of the present invention to fibrous material contain as a rule 1 to 30 percent by weight of at least one compound of formula (1) and optionally 1 to 30 percent by weight of (a) monomeric compounds of formula (8) or of (b) at least one homopolymer derived from the monomers of formulae (9) to (11) or of (c) further homo- or copolymers. These percentages by weight are based on the total weight of the preparations or compositions. The total weight of the compounds of formula (1), the other monomers and the further homo- and copolymers in the preparations, should not exceed 60 percent by weight, preferably 40 percent by weight.

The preparations for providing synthetic organic material with an antistatic and dirt repellent finish contain, for example, 1 to 30, in particular 1 to 20 and preferably 1 to 10, percent by weight of at least one compound of formula (1) and 1 to 10, preferably 1 to 5, percent by weight of at least one compound of formula (8), in particular of formulae (8a) or (8b), or they contain in addition to the compound of formula (1) 1 to 30, preferably 1 to 20, percent by weight of at least one homopolymer obtained from monomers of the formulae (9) to (11), or they contain in addition to the compound of formula (1) 1 to 30 percent by weight of further homo- or copolymers.

Suitable types of synthetic organic textile material that can be treated with the monomeric or polymeric compounds are those, for example, obtained from polyamides, polyesters, polyacrylonitrile or polyolefins. It is also possible to finish with advantage blends of these materials, optionally together with other fibres, for example cotton or wool. The textiles can be in the form of threads, fibres, flocks, non-wovens, woven or knitted fabrics or of piece goods, for example floor coverings, or other domestic textiles, such as upholstery fabrics, furnishing materials, curtains or wall coverings. The textile materials can be undyed or dyed by known methods.

The preparations or compositions which contain the monomeric or polymeric compounds can be applied to the substrate in conventional known manner at room temperature or also at elevated temperature, or example at 20° to 40° C. The pH of the preparations can be about 2 to 10, preferably 5 to 8, and they can also contain further additives customarily used in textile finishing.

The substrates can be treated with solutions or emulsions of the monomeric or polymeric compounds. The monomers can be applied, for example, from a solution in an organic solvent to the textile material and, after evaporation of the solvent, fixed om the fabric by heat. Polymers can also be applied to the fabrics from suitable solvents. The fixation on the substrates can be effected, if desired, in the presence of conventional catalysts that split off acid, for example magnesium chloride or zinc nitrate.

Fabrics can be impregnated, for example, by the exhaustion process or on a padder that is charged with the preparation at room temperature. The impregnated material is subsequently dried at 80° to 200° C, preferably at 120° to 160° C.

Further methods of application are, for example, spraying, brushing, roller coating or slop-padding. The compounds of the present invention are applied to the substrate in amounts of 0.1 to 10, preferably of 0.5 to 5, percent by weight.

The textile material finished according to the invention is antistatic, i.e. it releases no troublesome electrical discharges on being touched or walked on. The antisoiling effect and also the fastness to rubbing and light and the soft handle are not impaired by the finish.

The finish also has good permanency, i.e. it is resistant to washes with conventional household detergents or to cleaning with customary organic solvents. Carpeting materials, for example, can be repeatedly brushed, vacuum cleaned or shampooed without any loss of the finishing effects.

The following Examples illustrate the present invention in more detail without implying any restriction to what is described therein. The parts and percentages are by weight unless otherwise indicated.

EXAMPLE 1

105.5 g (0.5 mole) of methylol-β-dimethoxyphosphonopropionic acid amide and 120.5 g (0.5 mole) of cetylamine are dissolved in 1000 ml of dioxan and heated for 10 hours to 100° C (reflux temperature). The solvent is subsequently distilled off in a water jet vacuum.

Yield: 224 g(= 99%) of a wax-like compound of formula

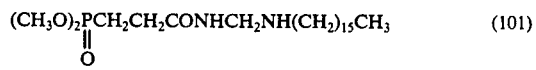

Analysis: calculated: N 6.45; P 7.12; found: N 6.22; P 7.52
Mass spectrum: M = 434 (theoretical value: 434).

EXAMPLE 2

105.5 g (0.5 mole) of methylol-β-dimethoxyphosphonopropionic acid amide and 134.5 g (0.5 mole) of stearylamine are reacted as described as described in Example 1.
Yield: 229 g(= 99.1%) of a wax-like compound of formula

Analysis: calculated: N 6.06; P 6.70; found: N 5.95; P 6.70
Mass spectrum: M 462 = (theoretical value: 462).

EXAMPLE 3

105.5 g (0.5 mole) of methylol-β-dimethoxyphosphonopropionic acid amide and 92.5 g (0.5 mole) of laurylamine are reacted as described in Example 1.
Yield: 175.4 g (= 92.8%) of a wax-like compound of formula

Analysis: calculated: N 7.4; P 8.2; found: N 7.3; P 8.7
Mass spectrum: M = 378 (theoretical value: 378).

EXAMPLE 4

105.5 g (0.5 mole) of methylol-β-dimethoxyphosphonopropionic acid amide and 120.5 g (0.5 mole) of di-2-ethylhexylamine are reacted as in Example 1.
Yield: 188.5 g (= 95.7%) of a compound of formula

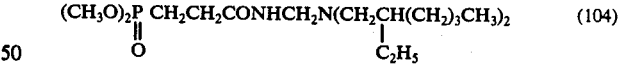

Analysis: calculated: N 6.45; P 7.12; found: N 6.22; P 6.4
Mass spectrum: M = 434 (theoretical value: 434).

EXAMPLE 5

133.5 g (0.5 mole) of methylol-β-diisopropoxyphosphonopropionic acid amide and 134.5 g (0.5 mole) of stearylamine are reacted as in Example 1.
Yield: 250 g(= 96.5%) of a compound of formula

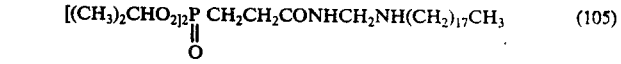

Analysis: calculated: N 5.04; P 5.97; found: N 5.5; P 6.1
Mass spectrum: M = 518 (theoretical value: 518).

EXAMPLE 6

133.5 g (0.5 mole) of methylol-β-diisopropoxyphosphonopropionic acid amide and 120.5 g of hexadecylamine (0.5 mole) are reacted as in Example 1.
Yield: 235 g (96%) of a compound of formula

[(CH₃)₂CHO]₂P CH₂CH₂CONHCH₂NH(CH₂)₁₅CH₃  (106)
‖
O

Analysis: calculated: N 5.71; P 6.31; found: N 5.7; P 6.5
Mass spectrum: M = 490 (theoretical value: 490).

EXAMPLE 7

133.5 g (0.5 mole) of methylol-β-diisopropoxyphosphonepropionic acid amide and 260.5 g (0.5 mole) of diesterarylamine are reacted as in Example 1.
Yield: 378 g (= 98.2%) of the compound of formula

[(CH₃)₂P CH₂CH₂CONHCH₂N[(CH₂)₁₇CH₃]₂  (107)
‖
O

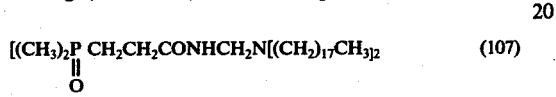

Analysis: calculated: N 3.63; P 4.02; found: N 3.8; P 3.9
Mass spectrum: M = 770 (theoretical value: 770).

EXAMPLE 8

73.5 g of phthalimide (0.5 mole) are reacted with 15 g of formaldehyde (0.5 mole) and 92.5 g (0.5 mole) of laurylamine in benzene at 80° C as in Example 1.
Yield: 168 (= 97.7%) of the compound of formula

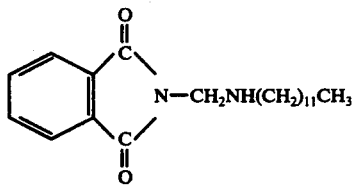
(108)

Analysis: calculated: N 8.14; found: N 8.0
Mass spectrum: M = 344 (theoretical value: 344).

EXAMPLE 9

73.5 g (0.5 mole) of phthalimide are reacted with 15 g (0.5 mole) of formaldehyde and 120.5 g (0.5 mole) of cetylamine as in Example 8.
Yield: 198 g (= 99%) of the compound of formula

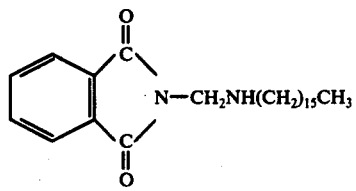
(109)

Analysis: calculated: N 7.0; found: N 7.3
Mass spectrum: M = 400 (theoretical value: 400).

EXAMPLE 10

73.5 g (0.5 mole) of phthalimide are reacted with 15 g (0.5 mole) of formaldehyde and 285.5 g of distearylamine as in Example 8. Toluene is used as solvent.
Yield: 332 g (= 97.1%) of the compound of formula

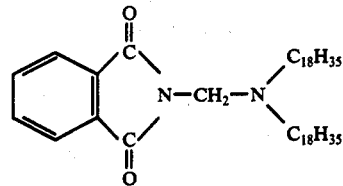

Analysis: calculated: N 4.4; found: N 4.2.

EXAMPLE 11

56.5 g (0.5 mole) of caprolactam are reacted with 15 g (0.5 mole) of formaldehyde and 92.5 g (0.5 mole) of laurylamine as in Exampe 8.
Yield: 146.6 g (= 94.7%) of the compound of formula

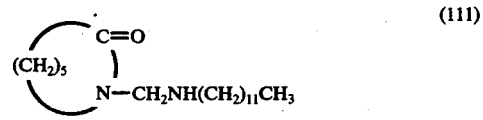
(111)

Analysis: calculated: N 9.02; found: N 8.75
Mass spectrum: M = 310 (theoretical value: 310).

EXAMPLE 12

56.5 (0.5 mole) of caprolactam are reacted with 15 g (0.5 mole) of formaldehyde and 176.5 g (0.5 mole) of dialurylamine as in Example 8. Toluene is used as solvent.
Yield: 210 g (= 92.5%) of the compound

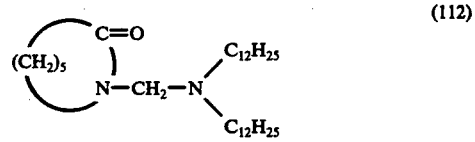
(112)

Analysis: calculated: N 5.85; found: N 6.0

EXAMPLE 13

56.5 g (0.5 mole) of caprolactam are reacted with 15 g (0.5 mole) of formaldehyde and 120.5 g (0.5 mole) of formaldehyde and 120.5 g (0.5 mole) of cetylamine as in Example 8. Toluene is used as solvent.
Yield: 178 g (= 97%) of the compound of formula

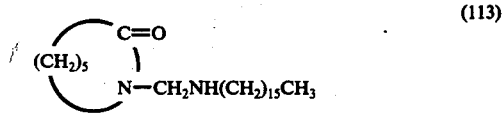
(113)

Analysis: calculated: N 7.64; found: N 7.1
Mass spectrum: M = 366 (theoretical value: 366).

EXAMPLE 14

49.5 g (0.5 mole) of succinimide are reacted with 15 g (0.5 mole) of formaldehyde and 92.5 g (0.5 mole) of laurylamine as in Example 8. Toluene is used as solvent.
Yield: 115 g (= 83.94%) of the compound of formula

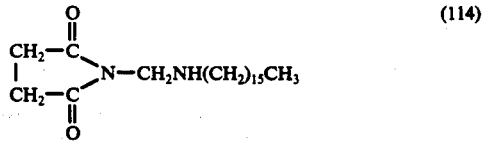
(114)

Analysis: calculated: N 9.45; found: N 9.2

EXAMPLE 15

49.5 g (0.5 mole) of succinimide are reacted with 15 g (0.5 mole) of formaldehyde and 120.5 g (0.5 mole) of cetylamine as in Example 8. Toluene is used as solvent. Yield: 176 g (= 100%) of the compound of formula

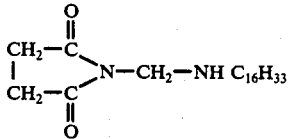 (115)

Analysis: calculated: N 7.95; found: N 7.2

EXAMPLE 16

98.5 g (0.5 mole) of laurinolactam are reacted with 15 g (0.5 mole) of formaldehyde and 92.5 g (0.5 mole) of laurylamine as in Example 8. Toluene is used as solvent. Yield: 197 g (= 100%) of the compound of formula

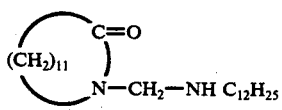 (116)

Analysis: calculated: N 7.1; found: N 7.5

EXAMPLE 17

211 g (1 mole) of N-methylol-β-methoxyphosphonopropionic acid amide are dissolved in 50 ml of water and the solution is treated with 85 g (1 mole) of methacrylic amide and 0.2 g of hydroquinone monomethyl ether. The reaction solution is adjusted to a pH of 3 with 1 ml of concentrated hydrochloric acid and then stirred for 6 hours at 50° C. After the reaction is terminated, the reaction solution is adjusted to a pH of 7 with 2 ml of normal sodium hydroxide solution and filtered. Yield: 340 g (= 100%) of a 84% solution of the compound of formula

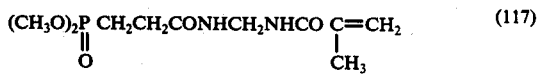 (117)

Analysis: calculated: P 11.0; found: P 11.0
Mass spectrum: M = 278 (theoretical value: 278).

EXAMPLE 18

133 g (0.5 mole) of N:methylol-β-diisopropoxyphosphonoic acid amide are reacted with 35.5 g (0.5 mole) of acrylic amide or 42.5 g (0.5 mole) of methacrylic amide as in Example 17, to give the compounds of formula

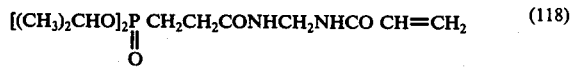 (118)

and

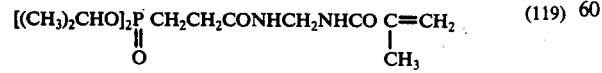 (119)

in 100% yield.

EXAMPLE 19

119.5 g (0.5 mole) of N-methylol-β-diethyloxyphosphonopropionic acid amide are reacted with 35.5 g (0.5 mole) of acrylic amide as in Example 17, to give the compound of formula

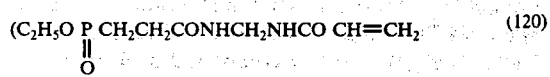 (120)

in 100% yield.

Analysis: calculated: P 10.6; found: P 10.3

EXAMPLE 20

85 g(1 mole) of methacrylic amide and 0.2 g of hydroxyquinone monomethyl ether are dissolved in 1000 ml of benzene. To this solution are added 30 g of paraformaldehyde. The solution is then heated to 40° C and a solution of 105 g (1 mole) of diethanolamine in 300 ml of benzene is added thereto in the course of about 2 hours. The reaction mixture is then kept for a further 5 hours at 60° C. After termination of the reaction the resultant compound precipitates as lower phase. It is separated and freed from residual solvent to give 178.5 g of a light yellow viscous compound of formula

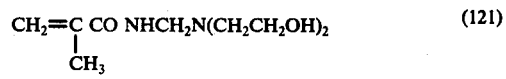 (121)

in 88.4% yield.

Analysis: calculated: N 13.85; found: N 13.4

EXAMPLE 21

Copolymer of isobutylacrylate/methylmethacrylate/methacrylic amide-N-methylolmonomethyl ether.

55.2 g (0.4 mole) of isobutylacrylate are dissolved in 150 ml of water and in the presence of 1 g of sodium laurylsulphate. The polymerisation is initiated by addition of 0.1 g of potassium persulphate. Then 10 g (0.1 mole) of methylmethacrylate are added in the course of 35 minutes and the polymerisation is continued for 4½ hours at 75° C. A solution of 2 g (0.015 mole) of methacrylic amide-M-methylolmonomethyl ether in 100 ml of water and 0.2 ; g of potasssium persulphate are then added and the polymerisation is brought to completion after a further 3 hours at 85° C.

Yield 314 g of a viscous emulsion with a solids content of 21%, corresponding to a polymer yield of 100%.

EXAMPLE 22

A preparation containing 20 g/l of the compound of formula (101) is padded at room temperature onto test substrates, which are squeezed out to a pick-up of 100%. The finished substrates are subsequently dried for 30 seconds at 170° C. The results of the antistatic and antisoiling effects of the finished substrates as well as the fastness to rubbing and the handle are reported in Table I.

Antisoiling:
  a. Grey Scale with the ratings 1 to 5 (5 = maximum rating),
  b. Determination of the whitening or greying of untreated material by reflexion measurement.

Fastness to rubbing: rating from 1 to 5 (5 = optimum rating).

Table I

| fibre | substrate | handle | antistatic effect | antisoil effect, dry treated | untreated |
|---|---|---|---|---|---|
| polyamide | fabric | medium soft | good | 9,3 (−) | 0 |
| polyacrylonitrile | fabric | medium soft | fairly good | 6,7 (−) | 0 |
| polyester | fabric | medium soft | very good | 4,2 (+) | 0 |
| polyester cotton (65/35) | fabric | medium soft | good | 3,5 (−) | 0 |

The antisoil effect of the finished fabric was assessed by method b).
(−) denotes whitening compared with untreated material
(+) denotes greying compared with untreated material.

EXAMPLE 23

Polyamide carpets are padded at room temperature with aqueous (unless otherwise indicated) liquors. The liquor pick-up is 100%. The carpets are subsequently dried for 10 minutes at 150° C.
The results are reported in Table II.
Preparations:
1. 50 g/l of the compound of formula (101).
2. 20 g/l of the compound of formula (106).
3. 50 g/l of the compound of formula (106).

Table II

| preparation | fastness to snubbing dry | wet | colour | handle | tendency to soil (compared with untreated material) | electrostatic behaviour resistance [Ω] | max. charge (in volts) |
|---|---|---|---|---|---|---|---|
| untreated | — | — | — | — | — | $10^{13}$ | 10000 |
| 1 | 2–3 | 1 | white | soft | more pronounced | $2,4.10^{11}$ | 1340–1850 |
| 2 | 4 | 4 | white | soft | more pronoucned | $1,8.10^{11}$ | 250–780 |
| 3 | 3 | 3 | white | soft | more pronounced | $9,3.10^{10}$ | 77–500 |

Preparations 1 to 3 contain the compounds of the present invention of formula (1).
A good antistatic effect is observed.

I claim:

1. Dialkylphosphonopropionic acid amides of formula

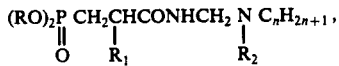

wherein R is straight-chain or branched alkyl of 1 to 8 carbon atoms, $R_1$ is hydrogen or methyl, $R_2$ is hydrogen or $C_nH_{2n+1}$ and $n$ is an integer from 1 to 24.

2. Compounds according to claim 1, wherein R is alkyl of 1 to 4 carbon atoms and $n$ is 1 or an integer from 6 to 24.

3. Compounds according to claim 2, wherein $R_2$ is hydrogen and $n$ is an integer from 6 to 18.

4. Compounds according to claim 3, wherein $R_1$ and $R_2$ are hydrogen and $n$ is an integer from 8 to 18.

5. A process for the manufacture of compounds of formula (a)

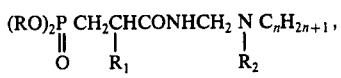

wherein R is straight-chain or branched alkyl of 1 to 8 carbon atoms, $R_1$ is hydrogen or methyl, $R_2$ is hydrogen or $C_nH_{2n+1}$ and $n$ is an integer from 1 to 24, which process comprises reacting compounds of formula (b)

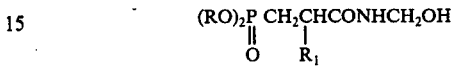

with mono- or dialkylamines which contain 1 to 24 carbon atoms in the alkyl moiety, at elevated temperature.

6. A process according to claim 5 for the manufacture of compounds of formula (a), wherein R is alkyl of 1 to 4 carbon atoms and $n$ is an integer from 6 to 24 which process comprises reacting compounds of formula (b), with monoalkylamines of 6 to 24 carbon atoms or with methylalkylamines that contain 6 to 24 carbon atoms in the alkyl moiety.

7. A process according to claim 5 for the manufacture of compounds of formula (a), wherein R is methyl or alkyl of 1 to 4 carbon atoms, $R_2$ is hydrogen and $n$ is an integer from 6 to 18, which process comprises reacting compounds of formula (b), with monoalkylamines of 6 to 18 carbon atoms.

8. A process according to claim 5 for the manufacture of compounds of formula (a), wherein R is methyl or alkyl of 1 to 4 carbon atoms, $R_1$ and $R_2$ are hydrogen and $n$ is an integer from 8 to 18, which comprises reacting compounds of formula (b), wherein $R_1$ is hydrogen, with monoalkylamines containing 8 to 18 carbon atoms.

9. A process according to claim 5, wherein the reaction is carried out at temperatures of 80° to 120° C.

* * * * *